(12) United States Patent
Seccomandi et al.

(10) Patent No.: US 10,759,780 B2
(45) Date of Patent: Sep. 1, 2020

(54) HINDERED AMINES

(71) Applicant: 3V Sigma S.P.A., Milan (IT)

(72) Inventors: Carlo Seccomandi, Bergamo (IT); Ferruccio Berte', Bergamo (IT); Ivan Balestra, Bergamo (IT)

(73) Assignee: 3V Sigma S.P.A., Milan (IT)

( * ) Notice: Subject to any disclaimer, the term of this patent is extended or adjusted under 35 U.S.C. 154(b) by 0 days.

(21) Appl. No.: 16/028,457

(22) Filed: Jul. 6, 2018

(65) Prior Publication Data

US 2019/0016702 A1    Jan. 17, 2019

(30) Foreign Application Priority Data

Jul. 11, 2017   (IT) .................. 102017000078234

(51) Int. Cl.
| | | |
|---|---|---|
| *C07D 401/14* | (2006.01) | |
| *C09K 15/30* | (2006.01) | |
| *C08K 5/3492* | (2006.01) | |

(52) U.S. Cl.
CPC ........ *C07D 401/14* (2013.01); *C08K 5/34926* (2013.01); *C09K 15/30* (2013.01)

(58) Field of Classification Search
None
See application file for complete search history.

(56) References Cited

U.S. PATENT DOCUMENTS

| 4,233,412 | A | 11/1980 | Rody et al. |
| 4,234,728 | A | 11/1980 | Rody et al. |
| 5,102,927 | A | 4/1992 | Rody et al. |
| 2018/0215898 | A1 * | 8/2018 | Weyland ............ C08K 5/34926 |

FOREIGN PATENT DOCUMENTS

| EP | 0399953 | A2 | 11/1990 |
| WO | 2015055563 | A1 | 4/2015 |

OTHER PUBLICATIONS

Search Report and Written Opinion of IT201700078234 dated Jan. 25, 2018.

* cited by examiner

*Primary Examiner* — Robert T Butcher
(74) *Attorney, Agent, or Firm* — Silvia Salvadori, P.C.; Silvia Salvadori

(57) ABSTRACT

Disclosed are triazine compounds characterised by ester pendants and polyalkylpiperidine pendants. The compounds according to the invention, either alone or mixed with other known agents, are useful as stabilisers of polymers, especially polyolefins.

11 Claims, No Drawings

HINDERED AMINES

This Non-Provisional Application claims priority to and the benefit of Italian Application No.: 102017000078234 filed on Jul. 11, 2017, the content of which is incorporated herein by reference in its entirety.

The present invention relates to polyalkylpiperidine triazine compounds which impart high stability to various kinds of polymer materials, especially polyolefins, towards oxidative action and photodegradation.

PRIOR ART

Polymers are known to be subject to deterioration due to the action of heat, light and oxygen; these factors cause loss of their mechanical properties, discolouring and other adverse effects.

In order to stabilise polymer materials, mainly towards the UV radiation in sunlight, various classes of compounds have been proposed, such as benzophenone and benzotriazole derivatives. The stability which these compounds give polymers is acceptable, but insufficient to meet current practical needs, especially in the case of fibres, films and raffia based on olefin polymers.

The polyalkylpiperidine derivatives commonly called HALS (hindered amine light stabilisers) are much more effective, and there are numerous patents relating to them.

Examples of HALS are described in U.S. Pat. No. 4,530,950, DE 1,929,928, U.S. Pat. Nos. 3,640,928, 4,477,615, 4,233,412, 4,331,586, DE 2,636,144, DE 2,456,864, U.S. Pat. Nos. 4,315,859, 4,104,248, 4,086,204, 4,038,280, 4,476,302, 4,981,964 and EP 2,632,914.

Synergistic mixtures of HALS are described in U.S. Pat. Nos. 4,692,486, 4,863,981, 5,021,485, EP 0709426, EP 0728806 and WO 2012/153260.

However, there is still a need for further compounds or mixtures that possess high stabilising efficacy towards polymer materials.

Particularly useful polyalkylpiperidine compounds are those wherein the active units based on hindered amines are present as pendants in molecules of triazine structure, because they possess a particular thermal stability suitable for their use, especially in plastic materials which must be processed at high temperatures.

In particular it is desirable to use stable triazine compounds such as those described above, but similar to the polymer matrices wherein they are incorporated. This characteristic is imparted to the compounds according to the present invention by the introduction of ester groups derived from mono- and dicarboxylic acids with a straight, cyclic or branched alkyl chain.

DESCRIPTION OF THE INVENTION

The present invention relates to novel triazine compounds wherein one pendant is ester and two pendants are polyalkylpiperidine.

Polymer compounds wherein the main chain is a polyester, and the polyalkylpiperidine units are part of the chain, are already known and widely used.

Stabilisers of this type, and their use as light stabilisers in polymers, are described, for example, in U.S. Pat. No. 4,233,412.

Trade names for this type of product, the CAS RN of which is 65447-77-0, are UVASORB HA22 (3V Sigma SpA), Tinuvin 622 (Base, Lowilite 62 (Addivant), Light Stabilizer 622 and UV-622.

However, in these compounds the activity of the polyalkylpiperidine groups can be partly reduced by the fact that the groups active for light stabilisation are blocked in the polymer chain.

It is therefore desirable to manufacture and use stabilising compounds containing ester groups wherein the groups active for stabilisation to radiation are bonded to the main chain as pendants, and therefore more mobile and able to perform a better stabilising action.

A first aspect of the invention relates to compounds of general formula (I):

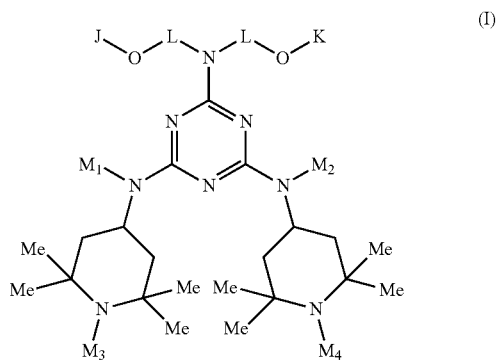

wherein

J and K are independently of one another hydrogen, a straight or branched $C_1$-$C_{22}$ acyl group or benzoyl, or an acyl group of formula (II):

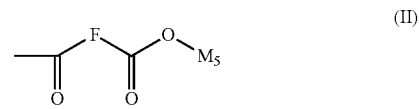

wherein:

F is a $C_1$-$C_{20}$ alkylene or $C_3$-$C_{10}$ cycloalkylene group optionally containing one or more unsaturations or an aromatic group, preferably a phenylene or naphthalene ring, $M_5$ is hydrogen or a saturated, unsaturated, straight or branched $C_1$-$C_{18}$ alkyl group or an aromatic group, on the proviso that J and K can never both be hydrogen, L is a $C_1$-$C_6$ alkylene or isoalkylene group, optionally unsaturated, $M_1$ and $M_2$, which may be the same or different, are hydrogen or $C_1$-$C_8$ alkyl, $M_3$ and $M_4$, which may be the same or different, are hydrogen or straight or branched $C_1$-$C_4$ alkyl groups or an —$OG_1$ group wherein $G_1$ is hydrogen or saturated, unsaturated, straight or branched $C_1$-$C_{10}$ alkyl.

The preferred compounds of Formula (I) are those wherein:

J and K are an acyl group defined by formula (II) wherein:

F is a straight $C_1$-$C_{20}$ alkylene group, $M_5$ is methyl or ethyl,

L is a —$CH_2$—$CH_2$—, —$CH_2$—$CH_2$—$CH_2$—, —CH($CH_3$)—$CH_2$—, or —$CH_2$—CH($CH_3$)— group, $M_1$ and $M_2$ are hydrogen or n-butyl, $M_3$ and $M_4$ are hydrogen or methyl.

The polypiperidine compounds of formula (I) can be prepared by a condensation reaction between an intermediate of general formula (III)

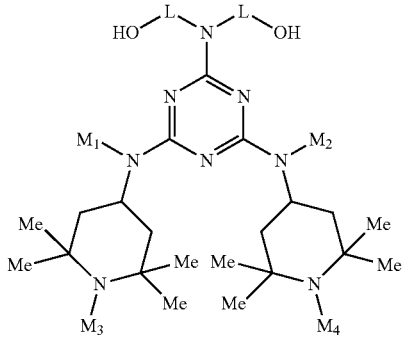

wherein:
L, $M_1$, $M_2$, $M_3$ and $M_4$ have the meanings previously described in formula (I) and C2-C20 carboxylic acids or benzoic acid or the corresponding esters or chlorides or compounds of formula (IV)

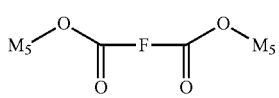

wherein:
$M_5$ and F have the meanings previously described in formula (II).

Examples of carboxylic acids and the corresponding esters or chlorides are acetic, caprylic, neodecanoic, lauric, myristic, palmitic, stearic and benzoic acids and the methyl and ethyl esters thereof and the chlorides thereof.

Examples of compounds of formula (IV) are:
dimethylesters, diethylesters, dibutylesters and dioctylesters or mixed esters of linear dicarboxylic acids such as propanedioic, butanedioic, hexanedioic, octanedioic, decanedioic and dodecanedioic acids.

dimethylesters, diethylesters, dibutylesters and dioctylesters or mixed esters of aromatic dicarboxylic acids such as terephthalic acids and phthalic acid.

dimethylesters, diethylesters, dibutylesters and dioctylesters of cycloalkane dicarboxylic acids such as 1,2-dicarboxycyclohexane, 1,3-dicarboxycyclohexane and 1,4-dicarboxycyclohexane.

The intermediates of formula (III) can easily be synthesised by well-known methods by reacting cyanuryl chloride with an equivalent of each of the compounds of formulas (V), (VI) and (VII) as described, for example, in JPS58152881:

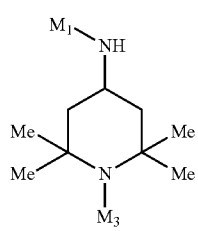

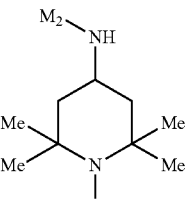

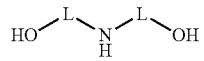

wherein L, $M_1$, $M_2$, $M_3$ and $M_4$ have the meanings described above in formula I.

The synthesis conditions of the compounds of formula (I) are those typical of the condensation reactions used to prepare esters from alcohols. A typical procedure for the preparation of the esters according to the invention consists of condensation of diols of formula (III) with mono- or dicarboxylic acids in the presence of suitable catalysts, with the removal of the water released during the esterification reaction. Similarly, the esters according to the invention can be obtained by condensation of diols of formula (III) with the esters of mono- or dicarboxylic acids, in the presence of suitable trans-esterification catalysts. In this case, the esterification reaction is conducted by removing the alcohols released during the reaction, which are generally low-boiling. The reaction is usually conducted at temperatures ranging between 50 and 300° C., preferably between 100 and 200° C., and at pressures ranging between 0 and 2 bars, preferably operating under vacuum.

The esters of formula (I) can be prepared in bulk or in the presence of suitable solvents inert to the esterification reaction. Examples of suitable solvents are saturated or aromatic hydrocarbons such as heptane, decane, toluene and xylene, ketones such as cyclohexanone and methyl-isobutylketone, and nitriles such as benzonitrile. Typical catalysts can be acids such as sulphuric acid, methanesulphonic acid and p-toluenesulphonic acid, bases such as lithium amide and sodium methylate, alkyl titanates such as tetraisopropyl titanate, and tin compounds such as dibutyltin oxide.

The esterification reactions are preferably conducted with a well-determined stoichiometric excess of the compound of formula (IV) and with high reaction conversions, with the aim of obtaining compounds containing ester groups at both ends.

The compounds of formula (I) are efficient light stabilisers for polymer materials, especially for polyolefins, either used alone or mixed with many other known stabilisers.

Examples of polymer materials which can be stabilised with the compounds and mixtures according to the present invention are polyethylene, polypropylene, polystyrene, polybutadiene, polyisoprene and the copolymers thereof, polyvinyl chloride, polyvinylidene chloride and the copolymers thereof, polyvinyl acetate and the copolymers thereof with ethylene; polyesters; polyamides, polyurethanes and polymer coatings and paints.

Mixtures of the compounds of formula (I) with other known stabilisers are also part of the invention.

Particularly important are the mixtures of the compounds of formula (I) with polymer compounds of formula (O)

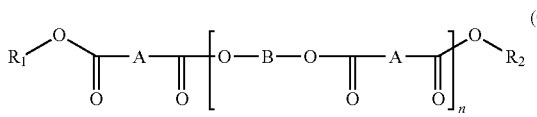

wherein:

n is an integer between 2 and 100

$R_1$ and $R_2$ are hydrogen or saturated, unsaturated, straight or branched $C_1$-$C_{18}$ alkyls or aromatic groups, A is a $C_1$-$C_{20}$ alkylene or $C_3$-$C_{10}$ cycloalkylene group optionally containing one or more unsaturations or an aromatic group;

wherein "aromatic group" preferably means a phenylene or naphthalene ring, and B is a group of formula (VIII)

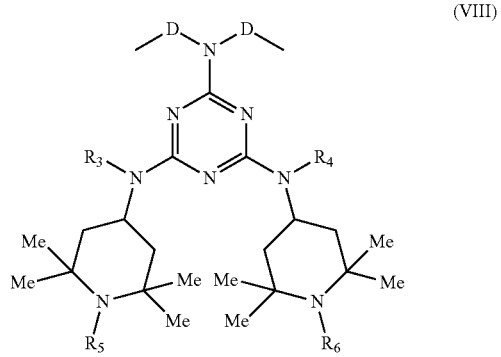

wherein:

D is a $C_1$-$C_6$ alkylene or isoalkylene group, optionally unsaturated, $R_3$ and $R_4$, which may be the same or different, are hydrogen or $C_1$-$C_8$ alkyl, $R_5$ and $R_6$, which may be the same or different, are hydrogen or straight or branched $C_1$-$C_4$ alkyl or an —$OG_1$ group wherein G is hydrogen or saturated, unsaturated, straight or branched $C_1$-$C_{10}$ alkyl. The compounds of formula O are described in Italian patent application 102017000073726 of 30 Jun. 2017.

The synthesis conditions of the compounds of formula (O) are those typical of the polycondensation reactions used to prepare polyesters. A typical procedure for the preparation of linear polyesters consists of polycondensation of diols with dicarboxylic acids in the presence of suitable catalysts, with the removal of the water released during the esterification reaction. Similarly, linear polyesters can also be obtained by polycondensation of diols and diesters of dicarboxylic acids in the presence of suitable trans-esterification catalysts. In this case, the polymerisation reaction is conducted by removing the alcohols released during the reaction, which are generally low-boiling. The reaction is usually conducted at temperatures ranging between 50 and 300° C., preferably between 100 and 200° C., and at pressures ranging between 0 and 2 bars, preferably operating under vacuum.

The polyesters can be prepared in bulk or in the presence of suitable solvents inert to the esterification reaction. Examples of suitable solvents are saturated or aromatic hydrocarbons such as heptane, decane, toluene and xylene, ketones such as cyclohexanone and methyl-isobutylketone, and nitriles such as benzonitrile. Typical catalysts can be acids such as sulphuric acid, methanesulphonic acid and p-toluenesulphonic acid, bases such as lithium amide and sodium methylate, alkyl titanates such as tetraisopropyl titanate, and tin compounds such as dibutyltin oxide.

The polymerisation reactions are conducted with an almost equimolar stoichiometric ratio between the reagents or with a slight excess of diester.

Moreover, mixtures of the compounds of formula (I) with at least one of the compounds of formula (P), (Q), (R), (S), (T) or (U) are preferred.

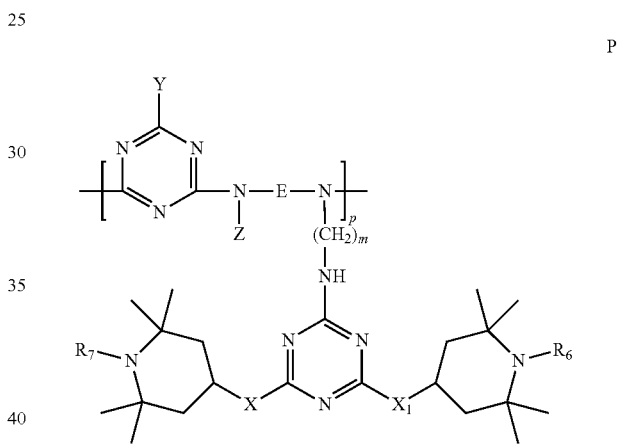

wherein p is between 3 and 20;

m is between 2 and 12;

$R_7$ and $R_8$, which may be the same or different, represent hydrogen, a straight or branched $C_1$-$C_{12}$ alkyl group, a $C_3$-$C_8$ alkenyl group or a $C_7$-$C_{19}$ aralkyl group; X and $X_1$, which may be the same or different, represent oxygen or a group of formula (IX)

wherein $R_9$ is hydrogen, a straight or branched $C_1$-$C_{12}$ alkyl group, a $C_5$-$C_{12}$ cycloalkyl group or a $C_7$-$C_{12}$ aralalkyl group;

E represents a —$(CH_2)_a$ group wherein a is between 2 and 12, on the proviso that a is different from m;

Z represents a $C_1$-$C_{18}$ alkyl group or a group of formula (X)

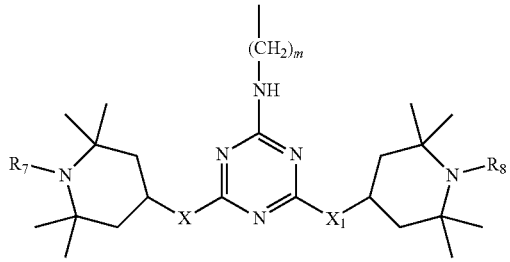
(X)

wherein m, X, $X_1$, $R_7$ and $R_8$ are as defined above, or a group of formula (XI)

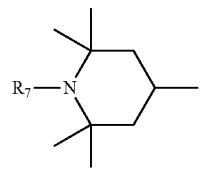
(XI)

wherein R7 is as defined above;

Y represents the O—$R_{11}$ and S—$R_{11}$ groups or a group of formula (XII)

(XII)

wherein $R_{10}$ and $R_{11}$, which may be the same or different, are hydrogen, a straight or branched $C_1$-$C_{18}$ alkyl group, a $C_5$-$C_{12}$ cycloalkyl group, a $C_7$-$C_{12}$ aralkyl group or a $C_6$-$C_{12}$ aryl group, or can form, together with the nitrogen atom to which they are bonded, a morpholino group or a $C_5$-$C_7$ heterocycle;

and the piperidino group (XIII)

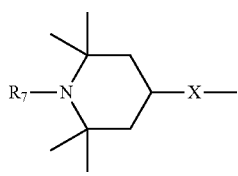
(XIII)

wherein $R_7$ and X are as defined above;

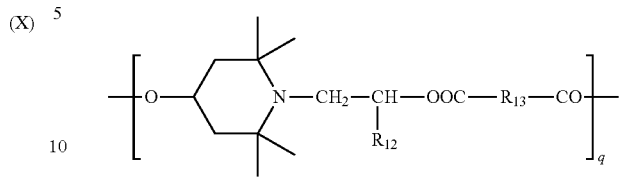
Q wherein
$R_{12}$ is hydrogen or methyl;
$R_{13}$ is a direct bond or a $C_1$-$C_{10}$ alkylene group;
q is an integer between 2 and 50;

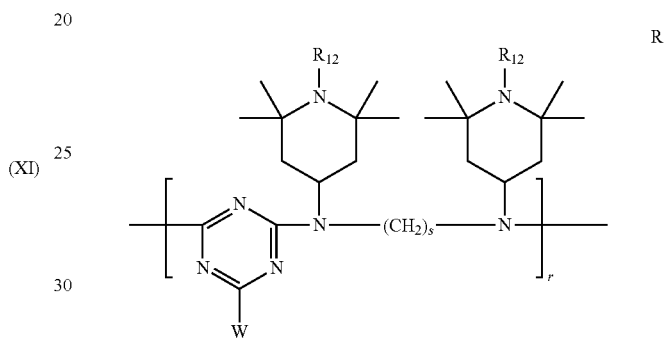
R wherein:
r is a number between 2 and 50
s is an integer between 2 and 10
$R_{12}$ is as defined above for the compounds of Formula Q;
W is a group of formula (XIV), (XV) or (XVI):

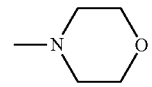
(XIV)

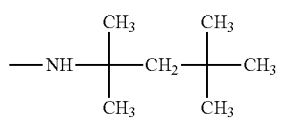
(XV)

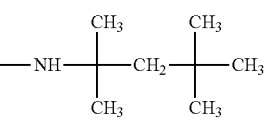
(XVI)

wherein:
$R_{14}$ is a straight or branched $C_1$-$C_4$ alkyl group;
$R_{12}$ is as defined above for the compounds of Formula R;

S $$R_{12}-N\underset{\phantom{|}}{\overset{\phantom{|}}{\bigcirc}}-O-OC-(CH_2)_t-CO-O-\underset{\phantom{|}}{\overset{\phantom{|}}{\bigcirc}}N-R_{12}$$

wherein:
t is an integer between 2 and 10;
$R_{12}$ is as defined above for the compounds of Formula R;

T $$R_{15}-NH-(CH_2)_3-\underset{R_{15}}{\overset{|}{N}}-(CH_2)_2-\underset{R_{15}}{\overset{|}{N}}-(CH_2)_3-NH-R_{15}$$

wherein:
$R_{15}$ represents the group of formula (XVII)

(XVII)

$$\underset{\underset{R_{17}}{|}}{\overset{\overset{R_{16}}{|}}{N-R_{16}}}$$

(triazine ring with N—R17 and N—R16 substituents)

wherein $R_{16}$ and $R_{17}$, independently of one another, are selected from the group formed by hydrogen, straight or branched $C_1$-$C_4$ alkyl groups and the group of formula (XVIII)

(XVIII)

$$R_{18}-N\underset{\phantom{|}}{\overset{\phantom{|}}{\bigcirc}}$$

wherein $R_{18}$ is hydrogen, a straight or branched $C_1$-$C_4$ alkyl group or an $OR_{19}$ group wherein $R_{19}$ is hydrogen or a straight or branched $C_1$-$C_8$ alkyl group;

U $$R_{15}-NH-(CH_2)_3-\underset{R_{15}}{\overset{|}{N}}-(CH_2)_2-\underset{R_{15}}{\overset{|}{N}}H$$

wherein $R_{15}$ has the meanings defined above for the compounds of formula T.

Said mixtures preferably contain 10% to 90% by weight of the compound of formula (I). More preferably, said mixtures contain 25% to 75% by weight of the compound of formula (I). Even more preferably, said mixtures contain 40% to 60% by weight of the compound of formula (I).

It has been observed that mixtures containing the compounds of formula (I), in particular with $M_1$ e $M_2$=n-butyl and F=—$(CH_2)_8$—, give polymer materials better stability against photodegradation and the oxidative action of air.

The compounds of formulas P, Q, R, S, T and U and the preparations thereof are known and described in U.S. Pat. No. 4,477,615, EP2632914, U.S. Pat. Nos. 3,840,494, 3,640,928, 4,331,586, EP93693, U.S. Pat. No. 4,263,434, JP57038589 and U.S. Pat. No. 6,046,304.

An example of a compound of formula P which can be used in the mixtures according to the invention is the product commercially known by the name of Uvasorb HA88 (3V Sigma S.p.A.).

Another example of a compound of formula P which can be used in the mixtures according to the invention is the product commercially known by the name of Uvasorb HA10 (3V Sigma S.p.A.).

An example of a compound of formula Q which can be used in the mixtures according to the invention is the product commercially known by the name of Uvasorb HA22 (CAS RN=65447-77-0).

An example of a compound of formula R, wherein W=residue of formula (XIV), which can be used in the mixtures according to the invention is the product commercially known by the name of Cyasorb UV-3346 (CAS RN=82451-48-7).

An example of a compound of formula R, wherein W=residue of formula (XV), which can be used in the mixtures according to the invention is the product commercially known by the name of Chimassorb 944 (CAS RN=71878-19-8).

An example of a compound of formula R, wherein W=residue of formula (XVI), which can be used in the mixtures according to the invention is the product commercially known by the name of Chimassorb 2020 (CAS RN=192268-64-7).

An example of a compound of formula S, wherein $R_{12}$=H and t=8, which can be used in the mixtures according to the invention is the product commercially known by the name of Uvasorb HA77 (CAS RN=52829-07-9).

An example of a compound of formula S, wherein $R_{12}$=methyl and t=8, which can be used in the mixtures according to the invention is the product commercially known by the name of Uvasorb HA29 (CAS RN=41556-26-7).

An example of a compound of formula T, wherein $R_{16}$=n-butyl and $R_{17}$=residue of formula (XVIII) having $R_{18}$=methyl, which can be used in the mixtures according to the invention is the product commercially known by the name of Chimassorb 119 (CAS RN=106990-43-6).

The mixtures according to the invention can be obtained by any known method, for example (a) by melting the compounds of formula (I) together with one or more of the compounds of formula (O), P, Q, R, S, T, and/or U, and then grinding or granulating the mixture obtained, (b) dissolving the ingredients in a common solvent and evaporating the solution until dry, or (c) incorporating the compounds separately in the polymer substrate to be stabilised, thereby obtaining the mixture in situ.

A further subject of the invention is the use of the compounds of formula (I) alone, mixed together or mixed with at least one of the compounds of formula (O), P, Q, R, S, T or U as stabilisers for polymers, in particular for polyolefin polymers.

According to the invention, the polymers comprise polyethylene, polypropylene, polystyrene, polybutadiene, polyisoprene and the copolymers thereof, polyvinyl chloride, polivinylidene chloride and the copolymers thereof, polyvinyl acetate and the copolymers thereof, in particular with ethylene; polyesters such as polyethylene terephthalate; polyamides such as Nylon 6 or 6,6; polyurethanes, coatings and polymer-based paints.

The compounds according to the invention and the mixtures according to the invention can be incorporated in the polymers by any known method for mixing additives and polymer materials; for example by:

mixing with the polymer, which can be in the form of a powder or granulate, in a suitable mixer;

addition in the form of a solution or suspension in a suitable solvent, and subsequent removal of the solvent from the polymer, which may be in the form of a powder, granulate or suspension, after thorough mixing;

addition to the polymer during its preparation, for example during the last stage of preparation.

The mixtures according to the invention can be added together with other types of stabilisers and additives generally used in the art, such as antioxidants based on phenols, amines or phosphites; UV radiation absorbers based on benzophenones or benzotriazoles; nickel-based stabilisers; plasticisers, lubricants, antistatic agents, flame retardants, corrosion inhibitors, metal deactivators and mineral fillers such as titanium dioxide, aluminium oxide and the like.

Examples of said additives are:

1. Antioxidants 1.1. Alkylated phenols, such as: 2,6-di-tert-butyl-4-methylphenol; 2-tert-butyl-4,6-di-methylphenol; 2,6-di-tert-butyl-4-ethylphenol; 2,6-di-tert-butyl-4-butylphenol; 2,6-di-tert-butyl-4-isobutylphenol; 2,6-di-cyclopentyl-4-methylphenol; 2-(α-methylcyclohexyl)-4,6-dimethylphenol; 2,6-di-octadecyl-4-methylphenol; 2,4,6-tricyclohexylphenol; 2,6-di-tert-butyl-4-methoxymethylphenol; straight and branched nonylphenols, such as 2,6-di-nonyl-4-methylphenol; 2,4-di-methyl-6-(1'-methylundecyl)phenol; 2,4-di-methyl-6-(1'-heptadecyl)-phenol and mixtures thereof.

1.2. Alkyl-thiomethylphenols, such as: 2,4-di-octyl-thiomethyl-6-tert-butylphenol; 2,4-di-octyl-thiomethyl-6-methylphenol; 2,4-di-octyl-thiomethyl-6-ethylphenol; 2,6-di-dodecylthiomethyl-4-nonylphenol.

1.3. Hydroquinones and alkylated hydroquinones, such as: 2,6-di-tert-butyl-4-methoxyphenol; 2,5-di-tert-butyl-hydroquinone; 2,5-di-tert-amyl-hydroquinone; 2,6-diphenyl-4-octadecyloxyphenol; 2,6-di-tert-butyl-hydroquinone; 2,5-di-tert-butyl-4-hydroxyanisole; 3,5-di-tert-butyl-4-hydroxyanisole; 3,5-di-tert-butyl-4-hydroxyphenyl stearate; bis(3,5-di-tert-butyl-4-hydroxyphenyl)adipate.

1.4. Tocopherols, such as α-tocopherol; γ-tocopherol; β-tocopherol; δ-tocopherol and mixtures thereof (vitamin E).

1.5. Hydroxylated thiodiphenyl ethers, such as: 2,2'-thiobis(6-tert-butyl-4-methylphenol); 2,2'-thiobis(4-octylphenol); 4,4'-thiobis(6-tert-butyl-3-methylphenol); 4,4'-thiobis(6-tert-butyl-2-methylphenol); 4,4'-bis(2,6-di-methyl-4-hydroxyphenyl)disulphide.

1.6. Alkylidene bisphenols, such as: 2,2'-methylenebis(6-tert-butyl-4-methylphenol); 2,2'-methylenebis(6-tert-butyl-4-ethylphenol); 2,2'-methylenebis(4-methyl-6-(α-methylcyclohexyl)phenol); 2,2'-methylenebis(4-methyl-6-cyclohexylphenol); 2,2'-methylenebis(6-nonyl-4-methylphenol); 2,2'-methylenebis-(4,6-di-tert-butylphenol); 2,2'-ethylidenebis-(4,6-di-tert-butylphenol); 2,2'-ethylidenebis(6-tert-butyl-4-isobutylphenol); 2,2'-methylenebis(6-(α-methylbenzyl)-4-nonylphenol); 2,2'-methylenebis(6-(α-ocdimethylbenzyl)-4-nonylphenol); 4,4'-methylenebis-(2,6-di-tert-butylphenol); 4,4'-methylenebis(6-tert-butyl-2-methyl-phenol); 1,1-bis(5-tert-butyl-4-hydroxy-2-methylphenyl)-butane; 2,6-bis(3-tert-butyl-5-methyl-2-hydroxybenzyl)-4-methylphenol; 1,1,3-tris-(5-tert-butyl-4-hydroxy-2-methylphenyl)-butane; 1,1-bis(5-tert-butyl-4-hydroxy-2-methylphenyl)-3-n-dodecyl-mercaptobutane; ethylene glycol bis(3,3-bis(3'-tert-butyl-4'-hydroxyphenyl)-butyrate); bis(2-(3'-tert-butyl-2'-hydroxy-5'-methylbenzyl)-6-tert-butyl-4-methylphenyl)-terephthalate; bis(3-tert-butyl-4-hydroxy-5-methylphenyl)-dicyclopentadiene; 1,1-bis-(3,5-dimethyl-2-hydroxyphenyl)butane; 2,2,bis-(3,5-di-tert-butyl-4-hydroxyphenyl)propane; 2,2-bis(5-tert-butyl-4-hydroxy-2-methylphenyl)-4-n-dodecyl-mercaptobutane; 1,1,5,5-tetra-(5-tert-butyl-4-hydroxy-2-methylphenyl)-pentane.

1.7. O-, N- and S-benzyl derivatives, such as: 3,5,3',5'-tetra-tert-butyl-4-4'-dihydroxydibenzyl ether; octadecyl-4-hydroxy-3,5-dimethylbenzyl-mercapto acetate; tridecyl-4-hydroxy-3,5-di-tert-butyl-benzylmercapto acetate; tri(3,5-di-tert-butyl-4-hydroxybenzyl)amine; bis(4-tert-butyl-3-hydroxy-2,6-dimethylbenzyl)dithioterephthalate; bis(3,5-di-tert-butyl-4-hydroxybenzyl)disulphide; isooctyl-3,5-di-tert-butyl-4-hydroxybenzylmercaptoacetate.

1.8. Malonates containing the hydroxybenzyl group, such as: dioctadecyl-2,2-bis-(3,5-di-tert-butyl-2-hydroxybenzyl) malonate; dioctadecyl-2-(3-tert-butyl-4-hydroxy-5-methylbenzyl)malonate; di-dodecylmercaptoethyl-2,2-bis-(3,5-di-tert-butyl-4-hydroxybenzyl)malonate; bis(4-(1,1,3,3-tetramethylbutyl)-phenyl)-2,2-bis-(3,5-di-tert-butyl-4-hydroxybenzyl)malonate.

1.9. Aromatic hydroxybenzyl compounds, such as: 1,3,5-tris-(3,5-di-tert-butyl-4-hydroxybenzyl)-2,4,6-trimethylbenzene; 1,4-bis-(3,5-di-tert-butyl-4-hydroxybenzyl)-2,3,5,6-tetramethylbenzene; 2,4,6-tris-(3,5-di-tert-butyl-4-hydroxybenzyl)-phenol.

1.10. Triazine derivatives, such as: 2,4-bis (octylmercapto)-6-(3,5-di-tert-butyl-4-hydroxyanilino)-1,3,5-triazine; 2-octylmercapto-4-6-bis(3,5-di-tert-butyl-4-hydroxyanilino)-1,3,5-triazine; 2-octylmercapto-4-6-bis(3,5-di-tert-butyl-4-hydroxyphenoxy)-1,3,5-triazine; 2,4,6-tris(3,5-di-tert-butyl-4-hydroxy-phenoxy)-1,3,5-triazine; 1,3,5-tris-(3,5-di-tert-butyl-4-hydroxybenzyl)-isocyanurate; 1,3,5-tris-(4-tert-butyl-3-hydroxy-2,6-dimethylbenzyl)isocyanurate; 2,4,6-tris(3,5-di-tert-butyl-4-hydroxyphenylethyl)-1,3,5-triazine; 1,3,5-tris-(3,5-di-tert-butyl-4-hydroxyphenylpropionyl)-hexahydro-1,3,5-triazine; 1,3,5-tris-(3,5-dicyclohexyl-4-hydroxybenzyl)isocyanurate.

1.11. Benzylphosphonates, such as: dimethyl-2,5-di-tert-butyl-4-hydroxybenzylphosphonate; diethyl-3,5-di-tert-butyl-4-hydroxybenzylphosphonate; dioctadecyl-3,5-di-tert-butyl-4-hydroxybenzylphosphonate; dioctadecyl-5-tert-butyl-4-hydroxy-3-methylbenzylphosphonate; the calcium salt of 3,5-di-tert-butyl-4-hydroxybenzylphosphonic acid monoethyl ester.

1.12. Acylaminophenols, such as lauric acid 4-hydroxyanilide, stearic acid 4-hydroxyanilide and octyl N-(3,5-di-tert-butyl-4-hydroxyphenyl)carbamate.

1.13. Esters of β-(3,5-di-tert-butyl-4-hydroxyphenyl)propionic acid with mono- or polyhydric alcohols, such as: methanol, ethanol, n-octanol, iso-octanol and octadecanol; 1,6-hexanediol; 1,9-nonanediol; ethylene glycol; 1,2-propanediol; neopentyl glycol; thiodiethylene glycol; diethylene glycol; triethylene glycol; pentaerythritol; tri-(hydroxyethyl)isocyanurate; N,N'-bis(hydroxyethyl)oxamide;

3-thioundecanol; 3-thiopentadecanol; trimethylhexanediol; trimethylolpropane; 4-hydroxymethyl-1-phospho-2,6,7-trioxabicyclo(2,2,2)octane.

1.14. Esters of β-(5-tert-butyl-4-hydroxy-3-methylphenyl)propionic acid with mono- or polyhydric alcohols, such as: methanol, ethanol, n-octanol, iso-octanol and octadecanol; 1,6-hexanediol; 1,9-nonanediol; ethylene glycol; 1,2-propanediol; neopentyl glycol; thiodiethylene glycol; diethylene glycol; triethylene glycol; pentaerythritol; tri-(hydroxyethyl)isocyanurate; N,N'-bis(hydroxyethyl)oxamide; 3-thioundecanol; 3-thiopentadecanol; trimethylhexanediol; trimethylolpropane; 4-hydroxymethyl-1-phospho-2,6,7-trioxabicyclo(2,2,2)octane.

1.15. Esters of β-(3,5-dicyclohexyl-4-hydroxyphenyl) propionic acid with mono- or polyhydric alcohols, such as: methanol, ethanol, n-octanol, iso-octanol and octadecanol; 1,6-hexanediol; 1,9-nonanediol; ethylene glycol; 1,2-propanediol; neopentyl glycol; thiodiethylene glycol; diethylene glycol; triethylene glycol; pentaerythritol; tri-(hydroxyethyl)isocyanurate; N,N'-bis(hydroxyethyl)oxamide; 3-thioundecanol; 3-thiopentadecanol; trimethylhexanediol; trimethylolpropane; 4-hydroxymethyl-1-phospho-2,6,7-trioxabicyclo(2,2,2)octane.

1.16. Esters of 3,5-di-tert-butyl-4-hydroxyphenyl acetic acid with mono- or polyhydric alcohols, such as: methanol, ethanol, n-octanol, iso-octanol and octadecanol; 1,6-hexanediol; 1,9-nonanediol; ethylene glycol; 1,2-propanediol; neopentyl glycol; thiodiethylene glycol; diethylene glycol; triethylene glycol; pentaerythritol; tri-(hydroxyethyl) isocyanurate; N,N'-bis(hydroxyethyl)oxamide; 3-thioundecanol; 3-thiopentadecanol; trimethylhexanediol; trimethylolpropane; 4-hydroxymethyl-1-phospho-2,6,7-trioxabicyclo(2,2,2)octane.

1.17. Amides of β-(3,5-di-tert-butyl-4-hydroxyphenyl) propionic acid, such as: N,N'-bis-(3,5-di-tert-butyl-4-hydroxyphenylpropionyl)-hexamethylenediamide; N,N'-bis-(3,5-di-tert-butyl-4-hydroxyphenylpropionyl)-trimethylenediamide; N,N'-bis-(3,5-di-tert-butyl-4-hydroxyphenylpropionyl)-hydrazide; N,N'-bis-(2-(3-(3,5-di-tert-butyl-4-hydroxyphenyl)propionyloxy)ethyl)-oxamide 1.18. Ascorbic acid (vitamin C).

1.19. Amine antioxidants, such as: N,N'-di-isopropyl-p-phenylenediamine; N,N'-di-sec-butyl-p-phenylenediamine; N,N'-bis(1,4-dimethylpentyl)-p-phenylenediamine; N,N'-bis(1-ethyl-3-methylpentyl)-p-phenylenediamine; N,N'-bis(1-methylheptyl)-p-phenylenediamine; N,N'-dicyclohexyl-p-phenylenediamine; N,N'-diphenyl-p-phenylenediamine; N,N'-bis-(2-naphthyl)-p-phenylenediamine; N-isopropyl-N'-phenyl-p-phenylenediamine; N-(1,3-dimethylbutyl)-N'-phenyl-p-phenylenediamine; N-(1-methylheptyl)-N'-phenyl-p-phenylenediamine; N-cyclohexyl-N'-phenyl-p-phenylenediamine, 4-(p-toluen-sulphamoyl)diphenylamine; N,N'-dimethyl-N,N'-di-sec-butyl-p-phenylenediamine; diphenylamine; N-allyl-diphenylamine; 4-isopropoxydiphenylamine, N-phenyl-1-naphthylamine; N-(4-tert-octylphenyl)-1-naphthylamine; N-phenyl-2-naphthylamine; p,p'-di-tert-octyl-diphenylamine; 4-n-butyl-aminophenol; 4-butyryl-aminophenol; 4-nonanoyl-aminophenol; 4-dodecanoyl-aminophenol; 4-octadecanoyl-aminophenol; bis(4-methoxyphenyl)amine; 2,6-di-tert-butyl-4-dimethylaminomethylphenol; 2,4'-diaminodiphenylmethane; 4,4'-diaminodiphenyl-methane; N,N,N',N'-tetramethyl-4,4'-diaminodiphenylmethane; 1,2-bis-((2-methylphenyl)-amino)ethane; 1,2-bis-(phenylamine)propane; o-tolyl-biguanide; bis-(4-(1',3'-dimethylbutyl)phenyl)amine; tert-octyl-N-phenyl-1-naphthylamine; mixtures of dialkylated tert-butyl/tert-octyl-diphenylamines; mixtures of mono- and di-alkyl nonyldiphenylamines; mixtures of mono- and di-alkyl dodecyldiphenylamines; mixtures of mono- and di-alkyl isopropyl/isohexyldiphenylamines; mixtures of mono- and di-alkyl tert-butyldiphenylamines; 2,3-dihydro-3,3-dimethyl-4H-1,4-benzothiazine; phenothiazine; mixtures of mono- and dialkyl tert-butyl/tert-octylphenothiazines, mixtures of mono- and dialkyl tert-octyl-phenothiazines; N-allylphenothiazine; N,N,N',N'-tetraphenyl-1,4-diamino-2-butene; N,N'-bis-(2,2,6,6-tetramethyl-piperidyl-4-hexamethylenediamine; bis(2,2,6,6-tetramethylpiperid-4-yl) sebacate; 2,2,6,6-tetramethylpiperid-4-one; 2,2,6,6-tetramethylpiperid-4-ol.

2. UV Radiation Absorbers and Light Stabilisers 2.1. 2-(2'-hydroxyphenyl)benzotriazoles, such as: 2-(2'-hydroxy-5-methylphenyl)benzotriazole; 2-(3',5'-di-tert-butyl-2'-hydroxyphenyl)benzotriazole; 2-(5'-tert-butyl-2'-hydroxyphenyl)benzotriazole; 2-(2'-hydroxy-5'-(1,1,3,3-tetramethylbutyl)-enyl)benzotriazole; 2-(3',5'-di-tert-butyl-2'-hydroxyphenyl)-5-chloro-benzotriazole; 2-(3'-tert-butyl-2'-hydroxy-5'-methylphenyl)-5-chloro-benzotriazole; 2-(3'-sec-butyl-5'-tert-butyl-2'-hydroxyphenyl)-benzotriazole; 2-(2'-hydroxy-4'-octyloxyphenyl)-benzotriazole; 2-(3',5'-di-tert-amyl-2'-hydroxyphenyl)benzotriazole; 2-(3',5'-bis-(α,α-dimethylbenzyl)-2'-hydroxyphenyl)benzotriazole; 2-(3'-tert-butyl-5'-(2-(2-ethylhexyloxy)-carbonylethyl)-2'-hydroxyphenyl)-5-chloro-benzotriazole; 2-(3'-tert-butyl-2'-hydroxy-5'-(2-octyloxycarbonylethyl)phenyl)-5-chloro-benzotriazole; 2-(3'-tert-butyl-2'-hydroxy-5'-(2-methoxycarbonylethyl)phenyl)-5-chloro-benzotriazole; 2-(3'-tert-butyl-2'-hydroxy-5'-(2-methoxycarbonylethyl)phenyl)-benzotriazole; 2-(3'-tert-butyl-2'-hydroxy-5'-(2-octyloxycarbonylethyl)phenyl)-benzotriazole; 2-(3'-tert-butyl-5'-(2-(2-ethylhexyloxy)-carbonylethyl)-2'-hydroxyphenyl)-benzotriazole; 2-(3'-dodecyl-2'-hydroxy-5'-methylphenyl)-benzotriazole; 2-(3'-tert-butyl-2'-hydroxy-5'-(2-isooctyloxycarbonylethyl)-phenylbenzotriazole; 2,2'-methylene-bis-(4-(1,1,3,3-tetramethylbutyl)-6-benzotriazol-2-ylphenol); the product of transesterification of 2-(3'-tert-butyl-5'-(2-methoxycarbonylethyl)-2'-hydroxyphenyl)-2H-benzotriazole with polyethylene glycol 300; (R—CH$_2$—CH$_2$—COO—CH$_2$—CH$_2$—)$_2$— wherein R can be: 3'-tert-butyl-4'-hydroxy-5'-2H-benzotriazol-2-ylphenyl; 2-(2'-hydroxy-3'-(α,α-dimethylbenzyl)-5'-(1,1,3,3-tetramethylbutyl)-phenyebenzotriazole; 2-(2'-hydroxy-3'-(1,1,3,3-tetramethylbutyl)-5'-(α,α-dimethylbenzyl)phenyl)benzotriazole.

2.2. 2-hydroxybenzophenones, such as the 4-hydroxy; 4-methoxy; 4-octyloxy; 4-decyloxy; 4-dodecyloxy; 4-benzyloxy; 4,2',4'-tri-hydroxy and 2'-hydroxy-4,4'-dimethoxy derivatives.

2.3. Esters of substituted and non-substituted benzoic acids, such as: 4-tertbutyl-phenyl-salicylate; phenyl salicylate; octylphenyl salicylate; dibenzoyl resorcinol; bis-(4-tert-butyl-benzoyl)-resorcinol; benzoyl resorcinol; 2,4-di-tert-butylphenyl 3,5-di-tert-butyl-4-hydroxybenzoate; hexadecyl 3,5-di-tert-butyl-4-hydroxybenzoate; octadecyl 3,5-di-tert-butyl-4-hydroxy-benzoate; 2-methyl-4,6-di-tert-butylphenyl 3,5-di-tert-butyl-4-hydroxybenzoate:

2.4. Acrylates, such as: ethyl α-cyano-β,β-diphenylacrylate; isooctyl α-cyano-β,β-diphenylacrylate; methyl α-arbomethoxycinnamate; methyl α-cyano-β-methyl-p-methoxycinnamate; butyl α-cyano-β-methyl-p-methoxycinnamate; methyl α-carbomethoxy-p-methoxycinnamate and N-(β-carbomethoxy-(β-cyanovinyl)-2-methylindoline.

2.5. Nickel derivatives, such as: 1:1 or 1:2 complexes of nickel with 2,2'-thio-bis-(4-(1,1,3,3-tetramethylbutyl)phenol, with or without binders such as n-butylamine, triethanolamine or N-cyclohexyldiethanolamine; nickel dibutylthiodicarbamate; nickel salts of 4-hydroxy-3,5-di-tert-butylbenzylphosphonic acid mono-alkyl esters (such as methyl or ethyl esters); nickel complexes with keto-oxime, for example with 2-hydroxy-4-methylphenyl undecyl-keto-oxime; nickel complexes with 1-phenyl-4-lauroyl-5-hydroxy-pyrazole, with or without additional binders.

2.6. Oxamides, such as: 4,4'-dioctyloxy-oxalanilide; 2,2'-diethoxy-oxalanilide; 2,2'-dioctyloxy-5,5'-di-tert-butyl-oxalanilide; 2,2'-didodecyloxy-5,5'-di-tert-butyl-oxalanilide; 2-ethoxy-2'-ethyloxy-oxalanilide; N,N'-bis(3-dimethylaminopropyl)-oxalanilide; 2-ethoxy-2'-ethyl-5,4'-di-tert-butyl-oxalanilide; mixtures of disubstituted n- and p-methoxy oxalanilides and mixtures of disubstituted o- and p-ethoxy oxalanilides.

2.7. 2-(2-hydroxyphenyl)-1,3,5-triazines, such as: 2,4,6-tris(2-hydroxy-4-octyloxyphenyl)-1,3,5-triazine; 2-(2-hydroxy-4-octyloxyphenyl)-4,6-bis(2,4-dimethylphenyl)-1,3,5-triazine; 2,4-bis(2-hydroxy-4-propyloxyphenyl)-6-(2,4-dimethylphenyl)-1,3,5-triazine; 2-(2-hydroxy-4-octyloxyphenyl)-4,6-bis-(4-methyl-phenyl)-1,3,5-triazine; 2-(2-hydroxy-4-dodecyloxyphenyl)-4,6-bis-(2-4-dimethylphenyl)-1,3,5-triazine; 2-(2-hydroxy-4-tridecyloxyphenyl)-4,6-bis-(2,4-dimethyl-phenyl)-1,3,5-triazine; 2-(2-hydroxy-4-(2-hydroxy-3-butyloxy-propoxy)phenyl)-4,6-bis(2,4-dimethyl)-1,3,5-triazine; 2-(2-hydroxy-4-(2-hydroxy-3-octyloxy-propoxy)-phenyl)-4,6-bis(2,4-dimethyl)-1,3,5-triazine; 2-(4-(dodecyloxy/tridecyloxy-2-hydroxypropoxy)-2-hydroxyphenyl)-4,6-bis(2,4-dimethylphenyl)-1,3,5-triazine; 2-(2-hydroxy-4-(2-hydroxy-3-dodecyloxypropoxy)phenyl)-4,6-bis(2,4-dimethylphenyl)-1,3,5-triazine; 2-(2-hydroxy-4-hexyloxy)phenyl-4,6-diphenyl-1,3,5-triazine; 2-(2-hydroxy-4-methoxyphenyl)-4,6-diphenyl-1,3,5-triazine; 2,4,6-tris(2-hydroxy-4-(3-butoxy-2-hydroxy-propoxy)phenyl-1,3,5-triazine; 2-(2-hydroxyphenyl)-4-(4-methoxyphenyl)-6-phenyl-1,3,5-triazine; 2-(2-hydroxy-4-(3-(2-ethylhexyl-1-oxy)-2-hydroxypropyloxy)phenyl)-4,6-bis(2,4-dimethylphenyl)-1,3,5-triazine.

2.8. Triazine derivatives, such as: diethylhexyl butamido triazone, ethylhexyl triazone, 2,4-bis-[4-[5-(1,1-dimethylpropyl)benzoxazol-2-yl]phenylimino]-6-[(2-ethylhexyl)imino]-1,3,5-triazine, tris-biphenyltriazine, bis-ethylhexyloxyphenol-methoxyphenyl-triazine.

3. Metal deactivators, such as: N,N'-diphenyloxamide; N-salicylal-N'-salicylol-hydrazine; N,N'-bis(salicylol)hydrazine; N,N'-bis-(3,5-di-tert-butyl-4-hydroxyphenylpropionyl)-hydrazine; 3-salicylolamino-1,2,4-triazole; bis(benzylidene)-oxalyl dihydrazide; oxalanilide; isophthaloyl dihydrazide; sebacoyl bisphenylhydrazide; N,N'-diacetyladipoyl dihydrazide; N,N'-bis(salicyloyl)oxalyl dihydrazide; N,N'-bis(salicyloyl)thiopropionyl dihydrazide.

4. Phosphites and phosphonites, such as: triphenyl phosphite; diphenyl alkyl phosphites; phenyl dialkyl phosphites; tris(nonylphenyl)phosphite; trilauryl phosphite; trioctadecyl phosphite; distearyl pentaerythritol diphosphite; tris(2,4-di-tert-butyl-phenyl) phosphite; diisodecyl pentaerythritol diphosphite; bis(2,4-di-tert-butylphenyl) phosphite; diisodecyl pentaerythritol diphosphite; bis(2,4-di-tert-butylphenyl) pentaerythritol diphosphite; bis(2,6-di-tert-butyl-4-methylphenyl)-pentaerythritol diphosphite; diisodecyloxy-pentaerythritol diphosphite; bis-(2,4-di-tert-butyl-6-methylphenyl)pentaerythritol diphosphite; bis(2,4,6-tris(tert-butylphenyl) pentaerythritol diphosphite; tristearyl sorbitol triphosphite; bis(2,4-di-tert-butyl-6-methylphenyl) methyl phosphite; bis(2,4-di-tert-butyl-6-methylphenyl) ethyl phosphite; 2,2',2''-nitrilo(triethyltris(3,3',5,5'-tetra-tert-butyl-1,1'-biphenyl-2,2'-idyl) phosphite); 2-ethylhexyl (3,3',5,5'-tetra-tert-butyl-1,1'-biphenyl-2,2'-idyl) phosphite); tetra(2,4-di-tert-butylphenyl) 4-4'-biphenylene diphosphonite.

5. Hydroxylamines, such as: N,N-dibenzylhydroxylamine; N,N-diethylhydroxylamine; N,N-dioctylhydroxylamine; N,N-dilaurylhydroxylamine; N,N-ditetradecylhydroxylamine; N,N-dihexadecyl-hydroxylamine; N,N-dioctadecylhydroxylamine; N-hexadecyl-N-octadecylhydroxylamine; N-heptadecyl-N-octadecylhydroxylamine; N,N-dialkylhydroxylamines derived from hydrogenated tallow amines 6. Nitrones, such as: N-benzyl-alpha-phenyl-nitrone; N-ethyl-alpha-methyl-nitrone; N-octyl-alpha-heptyl-nitrone; N-lauryl-alpha-undecyl-nitrone; N-tetradecyl-alpha-tridecyl-nitrone; N-hexadecyl-alpha-pentadecyl-nitrone; N-octadecyl-alpha-pentadecyl-nitrone; N-heptadecyl-alpha-heptadecyl-nitrone; N-octadecyl-alpha-hexadecyl-nitrone; nitrones derived from N,N-dialkylhydroxylamines obtained from hydrogenated tallow amines 7. Thiosynergistic derivatives such as dilauryl thiodipropionate or stearyl thiodipropionate.

8. Antiperoxide agents, such as: esters of thiodipropionic acid with lauryl, stearyl, myristyl or tridecyl alcohols; mercaptobenzimidazole or 2-mercapto-benzoimidazole zinc salt; zinc dibutyldithiocarbamate; dioctadecyl disulphide; pentaerythritol tetrakis(β-dodecylmercapto)propionate.

9. Polyamide stabilisers, such as: copper salts in combination with iodides and/or phosphorated compounds and bivalent manganese salts.

10. Basic co-stabilisers, such as: melamine; polyvinylpyrrolidone; dicyandiamide; triallylcyanurate; urea derivatives; hydrazine derivatives; amines; polyamides; polyurethanes; alkali metal and alkaline earth metal salts of higher fatty acids such as calcium stearate and zinc stearate; magnesium behenate; magnesium stearate; sodium ricinoleate; potassium palmitate; pyrocatechol antimony or zinc salts.

11. Nucleating agents, such as: inorganic substances such as talc; metal oxides such as titanium dioxide or magnesium oxide; phosphates, carbonates or sulphates or alkaline earth metal salts; organic compounds such as mono- or polycarboxylic acids and the salts thereof, such as 4-tert-butylbenzoic acid, adipic acid, diphenylacetic acid and sodium succinate; sodium benzoate; polymer compounds such as anionic copolymers.

12. Benzofuranones and indolinones, such as those described in U.S. Pat. Nos. 4,325,863; 4,338,244; 5,175,312; 5,216,052; 5,252,643; DE 4316611; DE 4316622; DE 4316876; EP 0589839; and EP 0591102; 3-(4-(2-acetoethoxy)phenyl)-5,7-di-tert-butyl-benzofuran-2-one; 5,7-di-tert-butyl-3-(4-(2-stearoyloxyethoxy)phenyl)-benzofuran-2-one; 3,3'-bis(5,7-di-tert-butyl-3-(4-(2-hydroxyethoxy)phenyl)benzofuran-2-one); 5,7-di-tert-butyl-3-(4-ethoxyphenyl)-benzofuran-2-one; 3-(4-acetoxy-3,5-dimethylphenyl)-5,7-di-tert-butyl-benzofuran-2-one; 3-(3,5-dimethyl-4-pivaloyloxyphenyl)-5,7-di-tert-butyl-benzofuran-2-one; 3-(2,3-di-methylphenyl)-5,7-di-tert-butyl-benzofuran-2-one.

13. Fillers and reinforcing agents, such as: calcium carbonate; silicates; fibreglass; asbestos; talc; kaolin; mica; barium sulphate; metal oxides and hydroxides, titanium dioxide in its various forms, and carbon black; graphite; wood flour, fibre flour or other natural products; synthetic fibres.

14. Other additives, such as: plasticisers, lubricants, emulsifiers, pigments and rheology modifiers; catalysts; flow control agents; optical brighteners; flame retardants; antistatic agents and swelling agents.

The quantity of mixtures according to the invention required for effective stabilisation of the polymer depends on a number of factors, such as the type and characteristics of the polymer, its intended use, the intensity of the radiation, and the duration of the likely exposure.

A quantity of mixture ranging from 0.01 to 5% by weight of the polymer, preferably 0.1 to 1.0%, is usually sufficient.

The examples below illustrate the invention in detail.

Example 1

Preparation of 2,2'-[[4,6-bis[butyl(2,2,6,6-tetramethyl-4-piperidinyl)amino]-1,3,5-triazin-2-yl]imino]bis-ethanol corresponding to the compound of formula III with $M_1=M_2=$butyl; $M_3=M_4=$H; $L=-(CH_2)_2-$ 300 g of xylene, 2.13 g of sodium hydrogen carbonate and 55.5 g of cyanuryl chloride are loaded into a 1 L flask under nitrogen. 72.0 g of N-butyl-2,2,6,6-tetramethylpiperidin-4-amine and 97.4 g of 18.5% aqueous $Na_2CO_3$ are added to the stirred mixture in sequence, maintaining the temperature at between 50 and 80° C., followed by a further 55.5 g of N-butyl-2,2,6,6-tetramethylpiperidin-4-amine and 97.4 g of 18.5% aqueous $Na_2CO_3$. The reaction is completed by maintaining a slight reflux for two hours, and the lower aqueous phase is then discharged. Maintaining the temperature at about 80° C., 43.5 g of diethanolamine and 96.1 g of 18.5% aqueous $Na_2CO_3$ are added. The mixture is brought to reflux, removing water with a Dean Stark apparatus. The mixture is kept under stirring at the same temperature for 6 h, and 150 g of xylene and 130 g of demineralised $H_2O$ are then added. The reaction mixture is stirred at 90-95° C. for 30 minutes, and the underlying aqueous phase is then discharged. After a further aqueous wash, the solvent and residual water are removed under vacuum. 182.1 g of product is obtained by solidifying the molten mass. UPLC-MS analysis gave an assay value=99.69%.

Example 2

Preparation of 2,2'-[[4,6-bis[butyl(1,2,2,6,6-pentamethyl-4-piperidinyeamino]-1,3,5-triazin-2-yl]imino]bis-ethanol corresponding to the compound of formula III with $M_1=M_2=$butyl; $M_3=M_4=$methyl; $L=-(CH_2)_2-$ 300 g of xylene, 2.13 g of $NaHCO_3$ and 55.5 g of cyanuryl chloride are loaded into a 1 L flask under nitrogen. 72.0 g of N-butyl-1,2,2,6,6-pentamethylpiperidin-4-amine and 97.4 g of 18.5% aqueous $Na_2CO_3$ are added to the stirred mixture in sequence, maintaining the temperature at between 50 and 80° C., followed by a further 55.5 g of N-butyl-1,2,2,6,6-pentamethylpiperidin-4-amine and 97.4 g of 18.5% aqueous $Na_2CO_3$. The reaction is completed by maintaining a slight reflux for two hours, and the lower aqueous phase is then discharged. Maintaining the temperature at about 80° C., 90.2 g of 30% aqueous formaldehyde and 46.1 g of 90% formic acid are added in about 2 hours. The reaction is completed at 85° C., then the mixture is cooled to 60° C. and 150 g of 10% aqueous NaOH is added. After mixing, the lower aqueous phase is discharged and the organic phase is washed with demineralised $H_2O$.

Maintaining the temperature at about 80° C., 42.8 g of diethanolamine and 96.1 g of 18.5% aqueous $Na_2CO_3$ are added. The mixture is brought to reflux, removing water with a Dean Stark apparatus. The mixture is maintained under stirring at the same temperature for 6 h, then 130 g of demineralised $H_2O$ is added. The reaction mixture is stirred at 90-95° C. for 30 minutes, and the underlying aqueous phase is then discharged. After a further aqueous wash, the solvent and residual water are removed under vacuum. 185.0 g of product is obtained by solidification of the molten mass. UPLC-MS analysis gave an assay value=99.52%

Example 3

Preparation of HALS1, corresponding to the compound of formula I wherein $L=-(CH_2)_2-$; $M_1=M_2=$butyl; $M_3=M_4=$H; $J=K=$ group of formula II wherein $F=-(CH_2)_2-$; $M_5=$methyl; obtainable by reacting 2,2'-[[4,6-bis[butyl(2,2,6,6-tetramethyl-4-piperidinyl)-amino]-1,3,5-triazin-2-yl]imino]bis-ethanol with a large excess on two moles of butanedioic acid 1,4-dimethyl ester.

20.0 g (137 mmols) of dimethyl succinate and 5.0 g (8.26 mmols) of triazine intermediate corresponding to the compound of formula III in example 1 are loaded into a 250 mL flask under nitrogen. The mixture is heated to 150° C., and 0.20 g of titanium (IV) isopropoxide is added to the molten mass. The temperature is gradually increased to 160° C., and the reaction is completed by removing under vacuum the methanol formed. 35 g of xylene is added and the catalyst is removed by hot aqueous washing. The organic phase is clarified by hot filtration. The xylene and the excess dimethyl succinate are removed under vacuum at 160° C. The molten mass is cooled to obtain 5 g of the HALS1 product in the form of yellow-brown flakes.

UPLC-MS analysis gave an assay value=94.91%.

Example 4

Preparation of HALS2, corresponding to the compound of formula I wherein $L=-(CH_2)_2-$; $M_1=M_2=$butyl; $M_3=M_4=$H; $J=K=$ group of formula II wherein $F=-(CH_2)_8-$; $M_5=$methyl; obtainable by reacting 2,2'-[[4,6-bis[butyl(2,2,6,6-tetramethyl-4-piperidinyl)-amino]-1,3,5-triazin-2-yl]imino]bis-ethanol with a large excess on two moles of decanedioic acid 1,10-dimethyl ester.

20.0 g (86.8 mmols) of dimethyl sebacate and 5.0 g (8.26 mmols) of triazine intermediate corresponding to the molecule of formula III in example 1 are loaded into a 250 mL flask under nitrogen. The mixture is heated to 150° C., and 0.20 g of titanium (IV) isopropoxide is added to the molten mass. The temperature is gradually increased to 160° C., and the reaction is completed by removing under vacuum the methanol formed. 35 g of xylene is added and the catalyst is removed by hot aqueous washing. The organic phase is clarified by hot filtration. The xylene and the excess dimethyl sebacate are removed under vacuum at 160° C. The molten mass is cooled to obtain 6.5 g of the HALS2 product in the form of a brown viscous liquid.

UPLC-MS analysis gave an assay value=94.03%.

Example 5

Preparation of HALS3, corresponding to the compound of formula I wherein $J=K=$benzoyl group with $M_1=M_2=$butyl; $M_3=M_4=$H; $L=-(CH_2)_2-$ obtainable by reacting 2,2'-[[4,6-bis[butyl(2,2,6,6-tetramethyl-4-piperidinyl)-amino]-1,3,5-triazin-2-yl]imino]bis-ethanol with a large excess on two moles of methyl benzoate. 20.0 g (147 mmols) of methyl benzoate and 5.0 g (8.26 mmols) of triazine intermediate corresponding to the compound of formula III in example 1 are loaded into a 250 mL flask under nitrogen. The mixture is heated to 150° C., and 0.20 g of titanium (IV) isopropoxide is added to the molten mass. The temperature is gradually increased to 160° C., and the reaction is completed by removing under vacuum the methanol formed. 35 g of xylene is added and the catalyst is removed by hot aqueous washing. The organic phase is clarified by hot filtration. The xylene and the excess methyl benzoate are removed under vacuum at 160° C. The molten mass is cooled to obtain 5 g of the HALS3 product in the form of a yellow solid.

UPLC-MS analysis gave an assay value=94.89%.

Example 6

Preparation of HALS4, corresponding to the compound of formula I wherein L=—$(CH_2)_2$—; $M_1=M_2$=butyl; $M_3=M_4$=methyl; J=K= group of formula II wherein F=—$(CH_2)_8$—; $M_5$=methyl; obtainable by reacting 2,2'-[[4,6-bis[butyl(1,2,2,6,6-pentamethyl-4-piperidinyl)-amino]-1,3,5-triazin-2-yl]imino]bis-ethanol with a large excess on two moles of decanedioic acid 1,10-dimethyl ester.

20.0 g (86.8 mmols) of dimethyl sebacate and 5.0 g (7.90 mmols) of triazine intermediate corresponding to the compound of formula III in example 2 are loaded into a 250 mL flask under nitrogen. The mixture is heated to 150° C., and 0.20 g of titanium (IV) isopropoxide is added to the molten mass. The temperature is gradually increased to 160° C., and the reaction is completed by removing under vacuum the methanol formed. 35 g of xylene is added and the catalyst is removed by hot aqueous washing. The organic phase is clarified by hot filtration. The xylene and the excess dimethyl sebacate are removed under vacuum at 160° C. The molten mass is cooled to obtain 5.2 g of the HALS4 product in the form of a brown viscous liquid.

UPLC-MS analysis gave an assay value=94.69%.

Application Examples

All quantities are expressed in weight unless otherwise stated.

Example 7

Light Stabilisation of Polypropylene Fibre 6 samples were prepared by the following procedure:

1000 parts by weight of unstabilised polypropylene homopolymer (fluidity index: about 10-12 g/10 min at 230° C.-2.16 kP) were mixed in a laboratory mixer with 1.0 parts by weight of calcium stearate, 0.50 parts by weight of tris-(2,4-di-tert-butyl-phenyl) phosphite, 0.50 parts by weight of 1,3,5-tris-(3,5-di-tert-butyl-4-hydroxybenzyl) isocyanurate, to five of which 1.5 parts by weight of stabilisers HALS1, HALS2, HALS3, HALS4 and HALS5 respectively were added, wherein HALS5 is a hindered polyester polymer amine containing the hindered amino groups inserted directly into the polymer chain identified by CAS RN=65447-77-0.

The dry mixtures thus obtained were extruded in a laboratory extruder at 230° C., and granulated after cooling of the extrusion.

The granulates were then converted to a film with a thickness of 100 microns, using a laboratory press by compression moulding at 210° C.

Specimens obtained from the various films were exposed in a Weather-Ometer Mod. Ci35A, according to ISO 4892 (T black panel 63±2° C., dry cycle). Specimens were taken periodically to undergo a Carbonyl Index test, using the FT-IR spectrophotometry technique. The increase in the value of the Carbonyl Index provides an indication of the state of photoxidative degradation of the material, and is correlatable with the loss of mechanical properties resulting from the photoxidation of the material.

The parameter used to compare the light resistance of the samples was $t_{0.10}$, defined as "exposure time in WOM, expressed in hours, on reaching a Carbonyl Index value of 0.10".

The experimental results obtained are summarised in the Table.

TABLE

Light stability of 100 micron PP film

| Stabilisation | $t_{0.10}$ |
|---|---|
| Without stabiliser | 720 |
| 0.15% HALS 1 | 1820 |
| 0.15% HALS 2 | 1900 |
| 0.15% HALS 3 | 1790 |
| 0.15% HALS 4 | 1850 |
| 0.15% HALS 5 | 1230 |

The results of this example clearly demonstrate that the hindered polymer amines according to the present invention, containing the hindered amino groups as a mobile pendant of the structure, are much more effective than those wherein the hindered amino group is inserted directly into a polymer chain.

The invention claimed is:

1. Compounds of general formula (I):

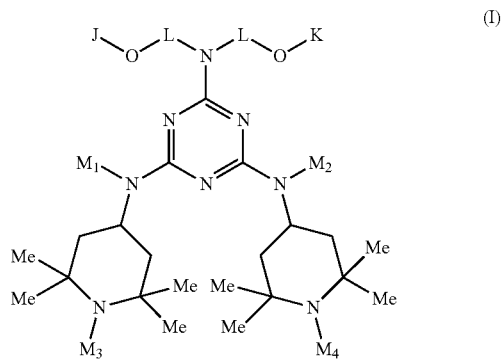

wherein:

J and K are an acyl group of formula (II):

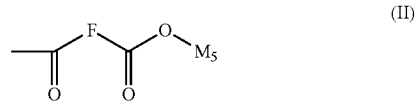

wherein:

F is a straight $C_1$-$C_{20}$ alkylene group $M_5$ is methyl or ethyl,

L is selected from a group consisting of —CH2-CH2-, —CH2-CH2-CH2-, —CH(CH3)-CH2- and —CH2-CH(CH3)-, $M_1$, $M_2$, which can be the same or different, are hydrogen or n-butyl, $M_3$, $M_4$, which can be the same or different, are hydrogen or methyl.

2. Compounds according to claim 1 wherein

J and K are an acyl group defined in formula (II)

wherein:

F is $(CH_2)_8$— group, $M_5$ is methyl,

L is selected from the group consisting of —CH2-CH2-, —CH(CH3)-CH2- and —CH2-CH(CH3)-, M1, M2, are n-butyl, M3, M4, are hydrogen or methyl.

3. Mixtures of compounds according to claim 1.

4. Mixtures according to claim 3, further comprising polymeric compounds of formula (O)

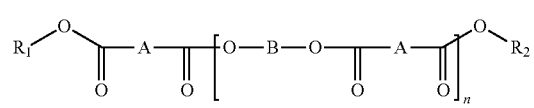
(O)

wherein:

n is an integer ranging from 2 to 100

$R_1$ and $R_2$ are hydrogen or straight or branched, saturated or unsaturated $C_1$-$C_{18}$, or aromatic groups;

A is a $C_1$-$C_{20}$ alkylene or $C_3$-$C_{10}$ cycloalkylene group, said group optionally containing one or more unsaturated or aromatic substituents;

and B is a group of formula (VIII)

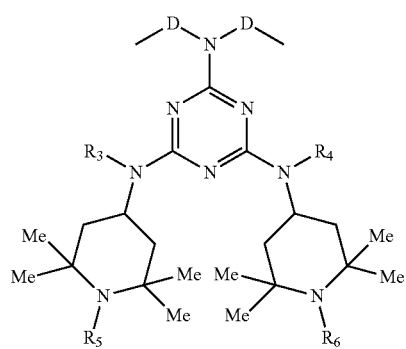
(VIII)

wherein:

D is an optionally unsaturated $C_1$-$C_6$ or iso $C_1$-$C_6$ group;

$R_3$, $R_4$, which can be the same or different, are hydrogen or $C_1$-$C_8$ alkyl;

$R_5$, $R_6$, which can be the same or different, are hydrogen or straight or branched $C_1$-$C_4$ alkyl or an —OG group wherein G is hydrogen or straight or branched, saturated or unsaturated, $C_1$-$C_{10}$.

5. Mixtures according to claim 3 further comprising at least one of the compounds of formula (P), (Q), (R), (S), (T) or (U)

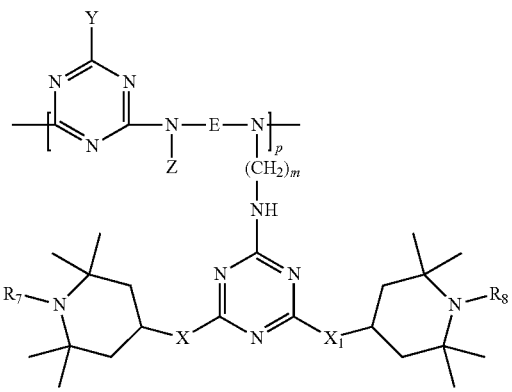
P wherein p ranges from 3 to 20;

m ranges from 2 to 12;

$R_7$ and $R_8$, which can be the same or different, are hydrogen, a straight or branched $C_1$-$C_{12}$ alkyl group, a $C_3$-$C_8$ alkenyl group or a $C_7$-$C_{19}$ aralkyl group;

X and $X_1$, which can be the same or different, are oxygen or a group of formula (IX)

(IX)

wherein $R_9$ is hydrogen, a straight or branched $C_1$-$C_{12}$ alkyl group, a $C_5$-$C_{12}$ cycloalkyl group or a $C_7$-$C_{12}$ aralkyl group;

E is a —$(CH_2)_a$— group wherein a ranges from 2 to 12, with the proviso that a is different from m;

Z is a $C_1$-$C_{18}$ alkyl group or a group of formula (X)

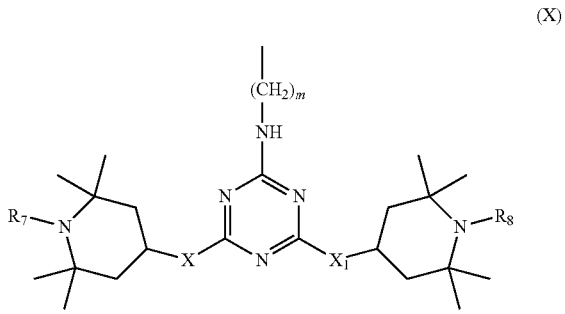
(X)

wherein m, X, $X_1$, $R_7$ and $R_8$ are as defined above, or a group of formula (XI)

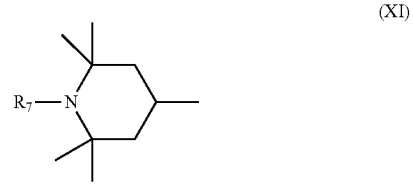
(XI)

wherein $R_7$ is as defined above;

Y is a O—$R_{11}$ and groups or a group of formula (XII)

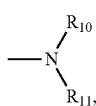
(XII)

wherein $R_{10}$ and $R_{11}$, which can be the same or different, are hydrogen, a straight or branched $C_1$-$C_{18}$ alkyl group, a $C_5$-$C_{12}$, cycloalkyl group, a $C_7$-$C_{12}$ aralkyl group or a $C_6$-$C_{12}$ aryl group or can form, together with the nitrogen atom to which they are bonded, a morpholino group or a $C_5$-$C_7$ heterocycle;

and a piperidino group (XIII)

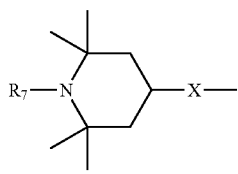
(XIII)

wherein $R_7$ and X are as defined above;

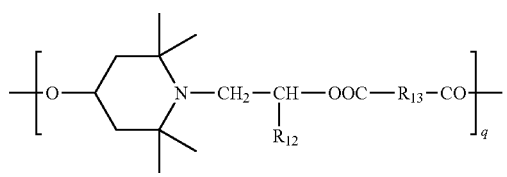
Q wherein $R_{12}$ is hydrogen or methyl;

$R_{13}$ is a direct bond or is a $C_1$-$C_{10}$ alkylene group;

q is an integer ranging from 2 to 50;

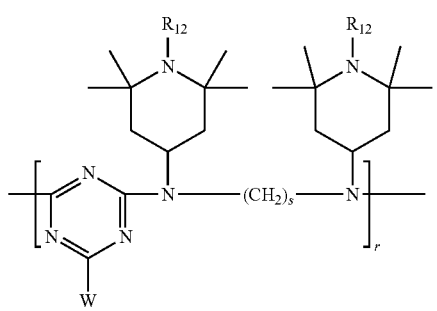
R wherein:

r is an integer ranging from 2 to 50, s is an integer ranging from 2 to 10, $R_{12}$ is as defined above for the compounds of formula Q;

W is selected from the group consisting of formula (XIV), (XV) and (XVI):

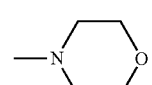
(XIV)

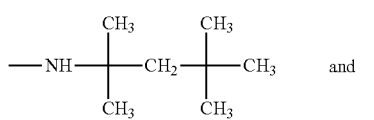
(XV)
and

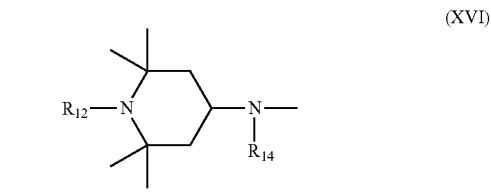
(XVI)

wherein:

$R_{10}$ is a straight or branched $C_1$-$C_4$ alkyl group;

$R_{12}$ is as defined above for the compounds of formula Q

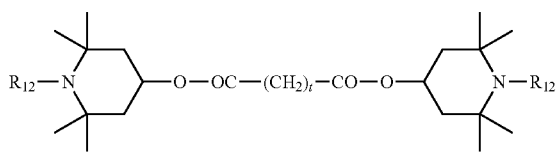
S wherein:

t is an integer ranging from 2 to 10;

$R_{12}$ is as defined above for the compounds of formula Q;

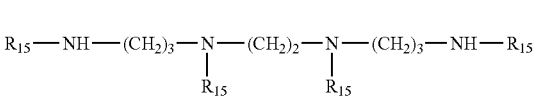
T wherein:

$R_{15}$ is the group of formula (XVII)

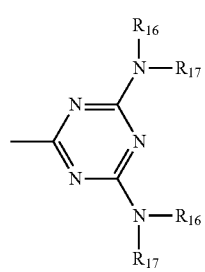
(XVII)

wherein $R_{16}$ and $R_{17}$, independently of one another, are selected from the group consisting of hydrogen, straight or branched $C_1$-$C_4$ alkyl groups and the group of formula (XVIII)

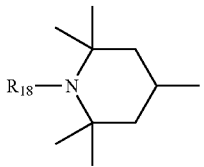

(XVIII)

wherein $R_{18}$ is hydrogen, a straight or branched $C_1$-$C_4$ alkyl group or an $OR_{19}$ group wherein $R_{19}$ is hydrogen or a straight or branched $C_1$-$C_8$ alkyl group;

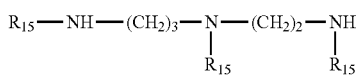

U wherein $R_{15}$ has the meanings defined above for the compounds of formula T.

6. Mixtures according to claim 3 comprising 10% to 90% by weight of the compounds of formula (I).

7. Mixtures according to claim 3 further comprising antioxidants; UV absorbers; nickel stabilisers; plasticisers, lubricants, antistatic agents, flame retardants, corrosion inhibitors, metal deactivators or mineral fillers.

8. Method of stabilizing polymers with the compounds according to claim 1.

9. Method of stabilizing polymers with the mixtures according to claim 3.

10. The method according to claim 8, wherein said polymer is selected from the group consisting of polyethylene, polypropylene, polystyrene, polybutadiene, polyisoprene and copolymers thereof, polyvinyl chloride, polyvinylidene chloride and copolymers thereof, polyvinyl acetate and copolymers thereof with ethylene; polyesters; polyamides, polyurethanes and polymers for coating and paint.

11. Mixtures according to claim 4, wherein A is a $C_1$-$C_{20}$ alkylene or $C_3$-$C_{10}$ cycloalkylene group optionally containing one or more unsaturations or a phenylene or naphthalene ring.

* * * * *